US010055538B2

(12) United States Patent
Majumdar et al.

(10) Patent No.: US 10,055,538 B2
(45) Date of Patent: Aug. 21, 2018

(54) PROCESSING OF SKIN CONDUCTANCE SIGNALS TO MITIGATE NOISE AND DETECT SIGNAL FEATURES

(71) Applicant: QUALCOMM Incorporated, San Diego, CA (US)

(72) Inventors: Somdeb Majumdar, San Diego, CA (US); Aniket A. Vartak, San Diego, CA (US); Robert S. Tartz, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 542 days.

(21) Appl. No.: 13/734,947

(22) Filed: Jan. 5, 2013

(65) Prior Publication Data

US 2014/0195163 A1 Jul. 10, 2014

(51) Int. Cl.
G01N 33/48 (2006.01)
G01N 33/50 (2006.01)
G06F 19/00 (2018.01)
A61B 5/00 (2006.01)
A61B 5/053 (2006.01)

(52) U.S. Cl.
CPC ............ *G06F 19/00* (2013.01); *A61B 5/0531* (2013.01); *A61B 5/7203* (2013.01)

(58) Field of Classification Search
None
See application file for complete search history.

(56) References Cited

U.S. PATENT DOCUMENTS

| 5,906,208 A | 5/1999 | Ishikawa et al. |
|---|---|---|
| 8,157,729 B2 | 4/2012 | Yang et al. |
| 2001/0040525 A1* | 11/2001 | Springer ................. G01S 7/021 342/195 |
| 2002/0116135 A1 | 8/2002 | Pasika et al. |
| 2007/0142873 A1* | 6/2007 | Esteller et al. ................. 607/45 |
| 2007/0213783 A1* | 9/2007 | Pless .................. A61N 1/36071 607/42 |

(Continued)

FOREIGN PATENT DOCUMENTS

| CN | 101637384 A | 2/2010 |
|---|---|---|
| JP | H08173407 A | 7/1996 |

(Continued)

OTHER PUBLICATIONS

Seizure, 2010, 2 pages. In Harvey Marcovitch (Ed.), Blacks medical dictionary, 42$^{nd}$ edition. Retrieved online on Oct. 12, 2014 from «http://www.credoreference.com».*

(Continued)

Primary Examiner — Russell Scott Negin
(74) Attorney, Agent, or Firm — Holland & Hart LLP

(57) ABSTRACT

Methods, systems, and devices are described for identifying noisy regions in a skin conductance signal. The signal is divided into a plurality of windows. Two or more features of the signal within a first window are computed. At least one of the two or more features being in a frequency domain. At least two of the features are combined to obtain at least a first metric. The first metric is compared to a corresponding threshold. The first window is identified as a noisy region of the skin conductance signal based on the comparison.

33 Claims, 14 Drawing Sheets

(56) References Cited

U.S. PATENT DOCUMENTS

| | | |
|---|---|---|
| 2007/0263978 A1 | 11/2007 | Yang et al. |
| 2008/0009685 A1 | 1/2008 | Kim et al. |
| 2009/0229171 A9 | 9/2009 | Storm |
| 2009/0281594 A1 | 11/2009 | King et al. |
| 2009/0326831 A1* | 12/2009 | McGonigle et al. ............ 702/19 |
| 2010/0022903 A1 | 1/2010 | Sitzman et al. |
| 2012/0296175 A1 | 11/2012 | Poh et al. |

FOREIGN PATENT DOCUMENTS

| | | |
|---|---|---|
| JP | 2005524464 A | 8/2005 |
| JP | 2014128433 A | 7/2014 |
| WO | WO-03094726 A1 | 11/2003 |
| WO | WO-2012092221 A1 | 7/2012 |

OTHER PUBLICATIONS

Alexander D.M., et al., "Separating individual skin conductance responses in a short interstimulus-interval paradigm", Journal of Neuroscience Methods, Elsevier Science Publisher B.V., Amsterdam, NL, vol . 146, No. 1, Jul. 15, 2005 (Jul. 15, 2005), pp. 116-123, XP027670326, ISSN: 0165-0270 [retrieved on Jul. 15, 2005] p. 117, section 1.2 "Previous methods of measurement" p. 119, section 2.4.1. "Segment extraction and peak detection" p. 120, col. 2, line 3—line 38; figure 2 p. 121, section 3.1 "Separating overlapping peaks", first paragraph.

International Search Report and Written Opinion—PCT/US2013/077060'ISA/EPO—dated May 30, 2014.

Plesnik E., et al., "ECG baseline drift correction through phase space for simple R-point detection", Computer-Based Medical Systems (CBMS), 2012 25th International Symposium on, IEEE, Jun. 20, 2012 (Jun. 20, 2012), pp. 1-4, XP032226937, DOI: 10.1109/CBMS.2012.6266307 ISBN: 978-1-4673-2049-8 p. 2, col. 2, paragraph 1.

Swangnetr M., et al., "Emotional State Classification in Patient Robot Interaction Using Wavelet Analysis and Statistics-Based Feature Selection", IEEE Transactions on Human-Machine Systems, IEEE, Piscataway, NJ, USA, vol. 43, No. 1, Dec. 2012 (Dec. 2012), pp. 63-75, XP011484268, ISSN: 2168-2291, DOI: 10.1109/TSMCA.2012.2210408 p. 69, col. 2.

* cited by examiner

PROCESSING OF SKIN CONDUCTANCE SIGNALS TO MITIGATE NOISE AND DETECT SIGNAL FEATURES

BACKGROUND

Mobile devices and wireless communication systems are widely deployed to provide various types of electronic communication content such as voice, data, and so on. While electronic forms of communication (e.g., email, text messages, voicemail, phone calls) have enabled people to conveniently contact and interact with others, the richness of electronic communications is attenuated.

Electronic communications, by themselves, do not generally convey the full emotional state of the sender. For example, research suggests that a small amount of emotional context in a given message is conveyed by the words (e.g., text in an electronic communications). A greater amount of the emotional context is conveyed vocally by the tone of the voice. An even greater amount is expressed using non-verbal communication, such as facial expression and other body gestures (Mehrabian, Albert; Ferris, Susan R. (1967). "Inference of Attitudes from Nonverbal Communication in Two Channels". *Journal of Consulting Psychology* 31 (3): 248-252). With regards to electronic communications, the emotional context or emotional state of the sender is commonly misinterpreted by the receiver.

Biopotential electrodes may be used with biosensors to collect physiological data from the human body. The physiological data may be used to determine an emotional state of a person. In addition, the biosensors may be used to monitor the physical health of a person. The biosensors may convert a biological response into an electrical signal. Typically, these electrodes that include biosensors are a standard shape and size (e.g., 8 mm flat disc). The electrical signals generated from the biological response are relatively small. As a result, even a small amount of noise may significantly interfere with the electrical signal. This may cause the determined emotional or physiological state of the person to be inaccurate or unknown.

A biopotential electrode with a large surface area may decrease the amount of noise that may cause interference with the electrical signals created by the biosensors, but using a biopotential electrode array with a large surface area may be impractical. On the other hand, a biopotential electrode with too small of a surface area may increase the amount of noise and render the reading of electrical signals associated with physiological data impractical.

SUMMARY

The described features generally relate to one or more improved systems, methods, and/or apparatuses for processing skin conductance signals. In one embodiment, the signals may be processed to identify noisy regions. The identified noisy regions may then be ignored when determining a skin conductance response (SCR) from the signals. In one configuration, the signals may also be processed to identify certain features, such as peaks of the signals. For example, the present systems and methods may process the skin conductance signals to identify primary and secondary peaks of the signals. The identification of these peaks may assist in determining an SCR. In one embodiment, a skin conductance signal may be processed to convert the signal from an energy domain to a time domain. This domain conversion may allow additional features of the signal to be identified and used in the determination of an SCR.

Methods, systems, and devices are described for identifying noisy regions in a skin conductance signal. The signal may be divided into a plurality of windows. Two or more features of the signal within a first window are computed. At least one of the two or more features being in a frequency domain. At least two of the features are combined to obtain at least a first metric. The first metric is compared to a corresponding threshold. The first window is identified as a noisy region of the skin conductance signal based on the comparison.

In one embodiment, the two or more features of the skin conductance signal include at least two of a normalized range, a normalized maximum or minimum, a number of mean crossings, an amount of low frequency energy, or an amount of high frequency energy. A skin conductance response (SCR) may be detected from the skin conductance signal, and the identified noisy region of the skin conductance signal may be ignored while detecting the SCR.

Each window may include a plurality of discrete samples of the skin conductance signal. At least one of the plurality of samples of the skin conductance signal may be included in both the first window and a second window, such that the second window overlaps the first window. At least one of the two or more features may be in a time domain.

Combining at least two of the features to obtain at least a first metric may include combining a first feature in the frequency domain with a second feature in the frequency domain. Computing two or more features of the signal within the first window may include computing an amount of low frequency energy and an amount of high frequency energy within the first window. Combining the at least two of the features to obtain at least the first metric may include forming a ratio of the amount of low frequency energy to the amount of high frequency energy.

In one embodiment, the corresponding threshold for the first metric may be identified from training data. The training data may be obtained from the skin conductance signal.

A value of at least one of the features may be compared to a corresponding at least one additional threshold, and the first window may be identified as a noisy region of the skin conductance signal based on a combination of the comparisons. Comparing a value of at least one of the features to a corresponding at least one additional threshold may include comparing a number of signal mean crossings to a corresponding mean crossing threshold, and identifying the first window as a noisy region of the skin conductance signal based on a combination of the comparisons.

In one example, computing two or more features of the signal within the first window may include computing an amount of low frequency energy and an amount of high frequency energy within the first window, and forming a ratio of the amount of low frequency energy to the amount of high frequency energy. In one configuration, the skin conductance signal may be acquired from a skin conductance sensor on-board a mobile device.

A mobile device for identifying noisy regions in a skin conductance signal is also described. The mobile device may include a processor and memory in electronic communication with the processor. Instructions may be stored in the memory. The instructions may be executable by the processor to divide the signal into a plurality of windows and compute two or more features of the signal within a first window. At least one of the two or more features being in a frequency domain. The instructions may also be executable by the processor to combine at least two or the features to obtain at least a first metric, compare the first metric to a corresponding threshold, and identify the first window as a noisy region of the skin conductance signal based at least in part on the comparison.

An apparatus for identifying noisy regions in a skin conductance signal is also described. The apparatus may include means for dividing the signal into a plurality of windows, and means for computing two or more features of the signal within a first window. At least one of the two or more features being in a frequency domain. The apparatus may also include means for combining at least two of the features to obtain at least a first metric, means for comparing the first metric to a corresponding threshold, and means for identifying the first window as a noisy region of the skin conductance signal based at least in part on the comparison.

A computer program product for identifying noisy regions in a skin conductance signal is also described. The computer program product may include a non-transitory computer-readable medium storing instructions executable by a processor to divide the signal into a plurality of windows, and compute two or more features of the signal within a first window. At least one of the two or more features being in a frequency domain. The instructions may be executable by the processor to combine at least two of the features to obtain at least a first metric, compare the first metric to a corresponding threshold, and identify the first window as a noisy region of the skin conductance signal based at least in part on the comparison.

A method to detect peaks of a skin conductance signal is also described. A first set of peaks may be identified by identifying a first set of one or more parameters of the skin conductance signal. The first set of peaks including one or more primary peaks of the skin conductance signal. Each parameter of the first set of one or more parameters may be compared to a corresponding threshold in a first set of one or more thresholds. A second set of one or more parameters of at least one primary peak may be computed in the first set of peaks. Each parameter of the second set of one or more parameters may be compared to a corresponding threshold in a second set of one or more thresholds. At least one secondary peak associated with the at least one primary peak may be identified based at least in part on the comparison of each parameter of the second set of one or more parameters to a corresponding threshold in the second set of one or more thresholds.

In one embodiment, the skin conductance signal may include a plurality of discrete samples. Computing the second set of one or more parameters may include computing a set of second derivatives for a set of discrete samples located along a first edge of a first primary peak, and determining, from the set of second derivatives, a curvedness factor of the first edge.

Determining the curvedness factor of the first edge may include determining a range of the set of second derivatives, and identifying a magnitude of the range as the curvedness factor. Comparing each parameter of the second set of one or more parameters to a corresponding threshold in a second set of one or more thresholds may include comparing the curvedness factor of the first edge to a curvedness threshold.

In one embodiment, a location of a secondary peak associated with the first primary peak may be identified based on a change in sign in the set of second derivatives. The first set of one or more parameters of the skin conductance signal may include at least one of a slope, a rise time, or an amplitude. The skin conductance signal may be acquired from a skin conductance sensor on-board a mobile device.

A mobile device for detecting peaks of a skin conductance signal is also described. The mobile device may include a processor and memory in electronic communication with the processor. Instructions may be stored in the memory. The instructions being executable by the processor to identify a first set of peaks by identifying a first set of one or more parameters of the skin conductance signal. The first set of peaks may include one or more primary peaks of the skin conductance signal. The instructions may also be executable by the processor to compare each parameter of the first set of one or more parameters to a corresponding threshold in a first set of one or more thresholds, compute a second set of one or more parameters of at least one primary peak in the first set of peaks, compare each parameter of the second set of one or more parameters to a corresponding threshold in a second set of one or more thresholds, and identify at least one secondary peak associated with the at least one primary peak based at least in part on the comparison of each parameter of the second set of one or more parameters to a corresponding threshold in the second set of one or more thresholds.

An apparatus for detecting peaks of a skin conductance signal is also described. The apparatus may include means for identifying a first set of peaks by identifying a first set of one or more parameters of the skin conductance signal. The first set of peaks including one or more primary peaks of the skin conductance signal. The apparatus also including means for comparing each parameter of the first set of one or more parameters to a corresponding threshold in a first set of one or more thresholds, means for computing a second set of one or more parameters of at least one primary peak in the first set of peaks, means for comparing each parameter of the second set of one or more parameters to a corresponding threshold in a second set of one or more thresholds, and means for identifying at least one secondary peak associated with the at least one primary peak based at least in part on the comparison of each parameter of the second set of one or more parameters to a corresponding threshold in the second set of one or more thresholds.

A computer program product for detecting peaks of a skin conductance signal is also described. The computer program product may include a non-transitory computer-readable medium storing instructions executable by a processor to identify a first set of peaks by identifying a first set of one or more parameters of the skin conductance signal. The first set of peaks including one or more primary peaks of the skin conductance signal. The instructions being executable by the processor to compare each parameter of the first set of one or more parameters to a corresponding threshold in a first set of one or more thresholds, compute a second set of one or more parameters of at least one primary peak in the first set of peaks, compare each parameter of the second set of one or more parameters to a corresponding threshold in a second set of one or more thresholds, and identify at least one secondary peak associated with the at least one primary peak based at least in part on the comparison of each parameter of the second set of one or more parameters to a corresponding threshold in a second set of one or more thresholds.

A method to convert a skin conductance signal from a time domain to an energy domain is also described. The skin conductance signal in the time domain may be divided into a plurality of windows. A function of the skin conductance signal in a first window may be computed to obtain a first metric of energy in the energy domain. A second signal may be computed in the energy domain. The second signal being a function of the metric of energy.

In one configuration, each window may include a plurality of discrete samples of the skin conductance signal. At least one of the plurality of discrete samples of the skin conductance signal may be included in overlapping windows of the plurality of windows. Computing the function of the skin conductance signal in the first window to obtain a first metric of energy in the energy domain may include computing an area defined at least in part by the first window and the skin conductance signal. The second signal may be compared to a corresponding threshold. A peak of the skin conductance signal may be identified in the energy domain based on the comparison.

The function of the skin conductance signal may be computed in a second window to obtain a second metric of energy in the energy domain. Dividing the skin conductance signal in the time domain into a plurality of windows may include adjusting a width of the second window to mitigate a variance between the first metric of energy and the second metric of energy. The skin conductance signal may be acquired from a skin conductance sensor on-board a mobile device.

A mobile device for converting a skin conductance signal from a time domain to an energy domain is also described. The device may include a processor and memory in electronic communication with the processor. Instructions may be stored in the memory. The instructions being executable by the processor to divide the skin conductance signal in the time domain into a plurality of windows, compute a function of the skin conductance signal in a first window to obtain a first metric of energy in the energy domain, and compute a second signal in the energy domain, the second signal being a function of the metric of energy.

An apparatus for converting a skin conductance signal from a time domain to an energy domain is also described. The apparatus may include means for dividing the skin conductance signal in the time domain into a plurality of windows, means for computing a function of the skin conductance signal in a first window to obtain a first metric of energy in the energy domain, and means for computing a second signal in the energy domain, the second signal being a function of the metric of energy.

A computer program product for converting a skin conductance signal from a time domain to an energy domain is also described. The computer program product including a non-transitory computer-readable medium storing instructions executable by a processor to divide the skin conductance signal in the time domain into a plurality of windows, compute a function of the skin conductance signal in a first window to obtain a first metric of energy in the energy domain, and compute a second signal in the energy domain, the second signal being a function of the metric of energy.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
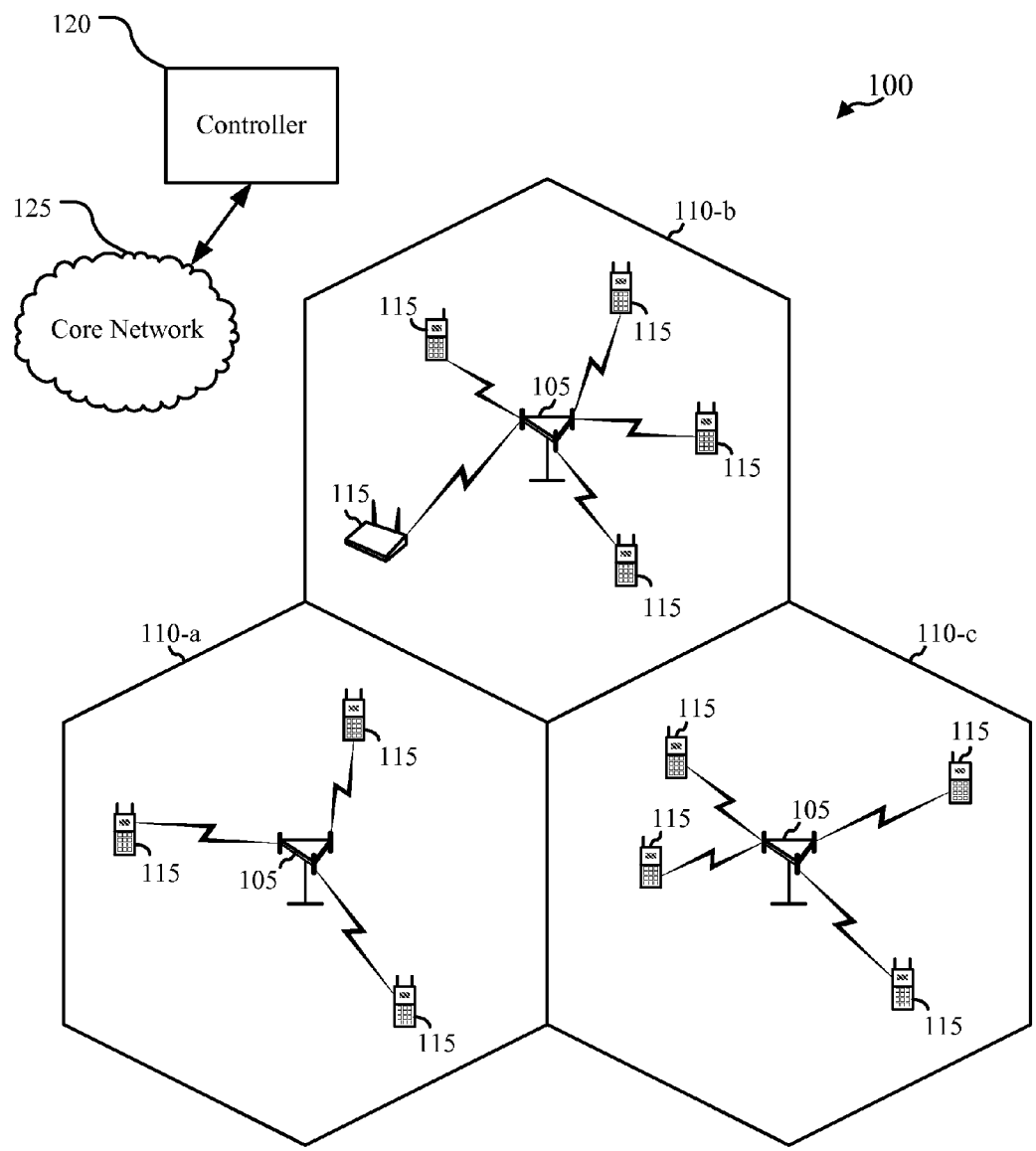
FIG. 1 is a block diagram of an example of a wireless communications system.

Various techniques for processing a skin conductance signal are described. A skin conductance signal is a signal that indicates the conductance of a subject's eccrine sweat glands. A skin conductance signal can be processed to generate a skin conductance response. A skin conductance response may provide useful physiological data about the subject, such as the subject's state of arousal. A subject may become aroused, for example, as a result of experiencing emotions such as attraction, excitement, or fear.

In one example of a processing technique described herein, a skin conductance signal is processed to identify noisy regions in the skin conductance signal. When detecting a skin conductance response from the skin conductance signal, the identified noisy regions can be ignored. In another example, a skin conductance signal is processed to detect features such as peaks of the skin conductance signal, and more particularly, primary and secondary peaks of the skin conductance signal. A secondary peak is a peak associated with a primary peak, such as a peak having a rising or falling edge subsumed by the falling or rising edge of a primary peak. In yet another example, a skin conductance signal is processed to convert the signal from a time domain to an energy domain. Converting the skin conductance signal to an energy domain sometimes enables the identification of signal features (e.g., peaks) that are not readily identifiable in the time domain.

The following description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, the methods described may be performed in orders different from those described, and various steps may be added, omitted, or combined. Also, features described with respect to certain embodiments may be combined in other embodiments.

The disclosed techniques for processing a skin conductance signal can be applied to skin conductance signals acquired by various means. However, the techniques are particularly well-suited for processing signals acquired by mobile devices. Mobile devices include cellular phones and wireless communications devices, such as smart phones, but may also include personal digital assistants (PDAs), tablets, other handheld devices, netbooks, or notebook computers. Mobile devices may also include biofeedback devices such as electrocardiograph (ECG or EKG) or electroencephalography (EEG) devices or sensors. Below, and by way of example, the disclosed techniques for processing a skin conductance signal are described in the context of mobile devices used in a wireless communication system.

Techniques described herein may be used by mobile devices capable of communicating with various wireless communications systems, such as cellular wireless systems, Peer-to-Peer wireless communications, wireless local access networks (WLANs), ad hoc networks, satellite communications systems, and other systems. The terms "system" and "network" are often used interchangeably. These wireless communications systems may employ a variety of radio communication technologies for multiple access in a wireless system such as Code Division Multiple Access (CDMA), Time Division Multiple Access (TDMA), Frequency Division Multiple Access (FDMA), Orthogonal FDMA (OFDMA), Single-Carrier FDMA (SC-FDMA), and/or other technologies. Generally, wireless communications are conducted according to a standardized implementation of one or more radio communication technologies called a Radio Access Technology (RAT). A wireless communications system or network that implements a Radio Access Technology may be called a Radio Access Network (RAN).

Examples of Radio Access Technologies employing CDMA techniques include CDMA2000, Universal Terrestrial Radio Access (UTRA), etc. CDMA2000 covers IS-2000, IS-95, and IS-856 standards. IS-2000 Releases 0 and A are commonly referred to as CDMA2000 1x, 1x, etc. IS-856 (TIA-856) is commonly referred to as CDMA2000 1xEV-DO, High Rate Packet Data (HRPD), etc. UTRA includes Wideband CDMA (WCDMA) and other variants of CDMA. Examples of TDMA systems include various implementations of Global System for Mobile Communications (GSM). Examples of Radio Access Technologies employing FDMA and/or OFDMA include Ultra Mobile Broadband (UMB), Evolved UTRA (E-UTRA), IEEE 802.11 (Wi-Fi), IEEE 802.16 (WiMAX), IEEE 802.20, Flash-OFDM, etc. UTRA and E-UTRA are part of Universal Mobile Telecommunication System (UMTS). 3GPP Long Term Evolution (LTE) and LTE-Advanced (LTE-A) are new releases of UMTS that use E-UTRA. UTRA, E-UTRA, UMTS, LTE, LTE-A, and GSM are described in documents from an organization named "3rd Generation Partnership Project" (3GPP). CDMA2000 and UMB are described in documents from an organization named "3rd Generation Partnership Project 2" (3GPP2). The techniques described herein may be used for the systems and radio technologies mentioned above as well as other systems and radio technologies.

Referring first to FIG. 1, a block diagram illustrates an example of a wireless communications system 100. The system 100 includes base stations 105 (or cells), mobile devices 115, a base station controller 120, and a core network 125 (the controller 120 may be integrated into the core network 125). The system 100 may support operation on multiple carriers (waveform signals of different frequencies).

The base stations 105 may wirelessly communicate with the mobile devices 115 via a base station antenna (not shown). The base stations 105 may communicate with the mobile devices 115 under the control of the base station controller 120 via multiple carriers. Each of the base station 105 sites may provide communication coverage for a respective geographic area. The coverage area for each base station 105 here is identified as 110-*a*, 110-*b*, or 110-*c*. The coverage area for a base station may be divided into sectors (not shown, but making up only a portion of the coverage area). The system 100 may include base stations 105 of different types (e.g., macro, micro, and/or pico base stations). There may be overlapping coverage areas for different technologies.

The mobile devices 115 may be dispersed throughout the coverage areas 110. The mobile devices 115 may be alternately referred to as mobile stations, access terminals (ATs), user equipments (UEs), subscriber stations (SSs), or subscriber units. The mobile devices 115 may include cellular phones and wireless communications devices, but may also include personal digital assistants (PDAs), other handheld devices, netbooks, notebook computers, etc.

The base stations 105 may allow users of the mobile devices 115 to communicate with each other. For example, a mobile device 115 may send electronic communications (e.g., email, text message, voicemail messages, etc.) to another mobile device. Users of different mobile devices 115 may also engage in real-time conversations (i.e., phone calls) using their respective devices. Still further, the mobile devices 115 may acquire skin conductance signals from their users, and may process these signals to detect skin conductance responses (e.g., physiological data about the users of the mobile devices 115, such as the arousals of the users).

Figure 2:
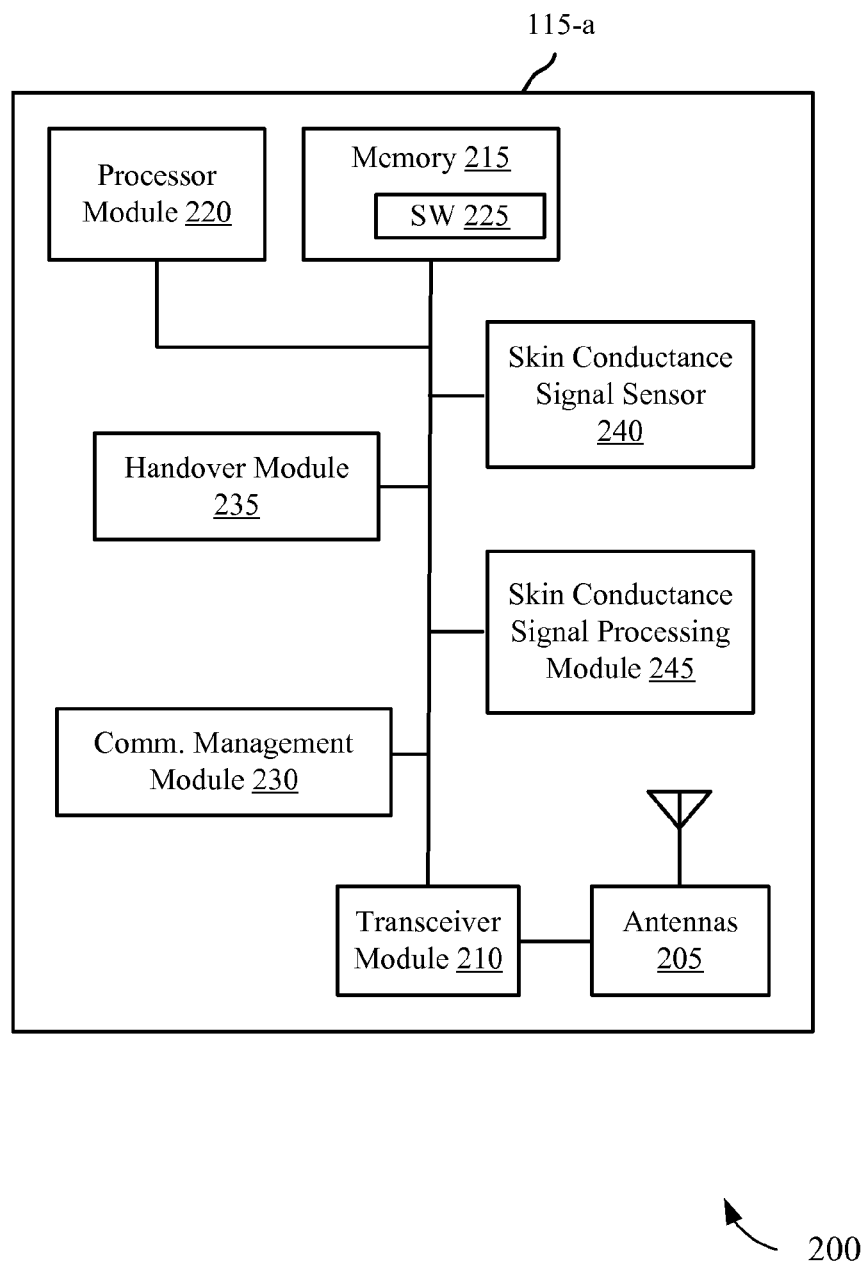
FIG. 2 is a block diagram of a first example of a mobile device providing skin conductance signal processing in accordance with various embodiments.

Turning now to FIG. 2, a block diagram 200 illustrates a mobile device 115-*a* providing skin conductance signal processing in accordance with various embodiments. The mobile device 115-*a* may have any of various configurations, such as personal computers (e.g., laptop computers, netbook computers, tablet computers, etc.), cellular telephones, PDAs, digital video recorders (DVRs), internet appliances, gaming consoles, e-readers, etc. The mobile device 115-*a* may have an internal power supply, such as a small battery, to facilitate mobile operation. In some embodiments, the mobile device 115-*a* may be an example of the mobile device 115 of FIG. 1. The mobile device 115-*a* may be a multi-mode mobile device.

The mobile device 115-*a* may include antennas 205, a transceiver module 210, memory 215, and a processor module 220, which each may be in communication, directly or indirectly, with each other (e.g., via one or more buses). The transceiver module 210 is configured to communicate bi-directionally, via the antennas 205 and/or one or more wired or wireless links, with one or more networks, as described above. For example, the transceiver module 210 may be configured to communicate bi-directionally with base stations 105 of FIG. 1. The transceiver module 210 may include a modem configured to modulate the packets and provide the modulated packets to the antennas 205 for transmission, and to demodulate packets received from the antennas 205. While the mobile device 115-*a* may include a single antenna, the mobile device 115-*a* will typically include multiple antennas 205 for multiple links.

The memory 215 may include random access memory (RAM) and read-only memory (ROM). The memory 215 may store computer-readable, computer-executable software code 225 containing instructions that are configured to, when executed, cause the processor module 220 to perform various functions. Alternatively, the software code 225 may not be directly executable by the processor module 220 but be configured to cause the computer (e.g., when compiled and executed) to perform functions described herein.

The processor module 220 may include an intelligent hardware device, e.g., a central processing unit (CPU) such as those made by Intel® Corporation or AMD®, a microcontroller, an application-specific integrated circuit (ASIC), etc. The processor module 220 may include a speech encoder (not shown) configured to receive audio via a microphone, convert the audio into packets (e.g., 30 ms in length) representative of the received audio, provide the audio packets to the transceiver module 210, and provide indications of whether a user is speaking. Alternatively, an encoder may only provide packets to the transceiver module 210, with the provision or withholding/suppression of the packet itself providing the indication of whether a user is speaking.

According to the architecture of FIG. 2, the mobile device 115-*a* may further include a communications management module 230. The communications management module 230 may manage communications with other mobile devices 115. By way of example, the communications management module 230 may be a component of the mobile device 115-*a* in communication with some or all of the other components of the mobile device 115-*a* via a bus. Alternatively, functionality of the communications management module 230 may be implemented as a component of the transceiver module 210, as a computer program product, and/or as one or more controller elements of the processor module 220.

In some embodiments, a handover module 235 may be utilized to perform reselection and handover procedures of the mobile device 115-*a* from one base station 105 to another. For example, the handover module 235 may perform a handover procedure of the mobile device 115-*a* from signaling carrier to another signaling carrier, a traffic carrier to another traffic carrier and between a signaling and traffic carrier.

In some embodiments, the device 115-*a* may include a skin conductance signal sensor 240. The sensor 240 may acquire a skin conductance signal for a user of the mobile device 115-*a*. The skin conductance signal sensor 240 may take the form of a single pair of electrodes embedded along a surface of the device 115-*a*. In other cases, the skin conductance signal sensor may include a configurable biopotential array of electrode tiles. The electrode tiles may be arranged in the array in different configurations and with different shapes. The array may be embedded along a surface area of the device 115-*a*. Biosensors may be incorporated with the electrodes to collect physiological data associated with the user of the device 115-*a*. Electrodes that are in contact with the skin of the user may be activated to begin collecting the data. For example, as the user holds the mobile device 115-*a* in his/her hand, the electrodes in contact with the skin of the user's hand, fingers, etc. may be activated. Activated electrodes may be deactivated after contact with the user's skin has terminated. For example, as the user changes the position of his/her grip of the device 115, the electrodes that are currently activated may be deactivated, and the electrodes that are currently deactivated may be activated. In one embodiment, the skin conductance signal may be acquired from skin conductance signal sensors 240 that may be worn by a user (e.g., one or more finger pads). Skin conductance signal sensors and configurable biopotential arrays of electrode tiles to acquire electrodermal activity are further disclosed in U.S. application Ser. No. 13/692,363 titled "Methods and Devices for Acquiring Electrodermal Activity," which is incorporated herein in its entirety by this reference.

A skin conductance signal processing module 245 may receive the skin conductance signal acquired by the skin conductance signal sensor 240 and perform on-board processing of the skin conductance signal. The skin conductance signal processing module 245 may process the skin conductance signal for a variety of purposes, using a variety of techniques, as described herein.

In some cases, the skin conductance signal may be acquired as, or converted to, a plurality of discrete samples. The samples may be provided directly to the skin conductance signal processing module 245, or may be stored in the memory 215 for subsequent retrieval. In some cases, some or all of the acquired samples may be associated with one or more timers. Upon expiration of the timer associated with a particular sample or sample set, the sample(s) may be cleared from the memory 215. In this manner, samples may be discarded when they are no longer relevant. The samples may also be cleared from the memory 215 in other ways.

Figure 3:
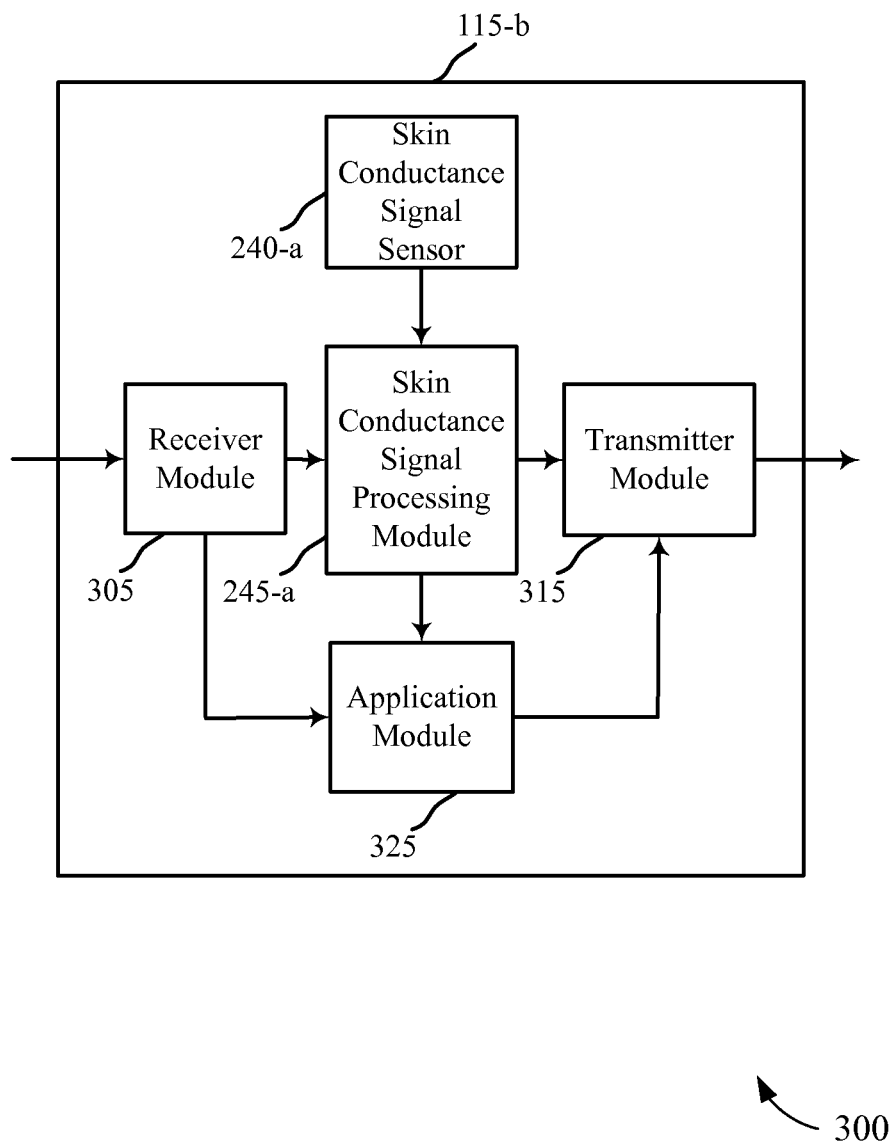
FIG. 3 is a block diagram of a second example of a mobile device providing skin conductance signal processing in accordance with various embodiments.

Referring now to FIG. 3, a block diagram 300 illustrates a mobile device 115-*b* that enables processing of skin conductance signals in accordance with various embodiments. The device 115-*b* may be an example of one or more aspects of mobile devices 115 described with reference to FIG. 1 and/or FIG. 2. The device 115-*b* may include a receiver module 305, a skin conductance signal processing module 245-*a*, a transmitter module 315, a skin conductance signal sensor 240-*a*, and/or an application module 325. Each of these components may be in communication with each other.

The components of the device 115-*b* may, individually or collectively, be implemented with one or more application-specific integrated circuits (ASICs) adapted to perform some or all of the applicable functions in hardware. Alternatively, the functions may be performed by one or more other processing units (or cores), on one or more integrated circuits. In other embodiments, other types of integrated circuits may be used (e.g., Structured/Platform ASICs, Field Programmable Gate Arrays (FPGAs), and other Semi-Custom ICs), which may be programmed in any manner known in the art. The functions of each unit may also be implemented, in whole or in part, with instructions embodied in a memory, formatted to be executed by one or more general or application-specific processors.

By way of example, the receiver module 305 may include one or more of a cellular receiver, a WLAN receiver, and a tactile receiver (e.g., a keyboard or touch screen). In some embodiments, the device 115-*b* may receive thresholds for use by the skin conductance signal processing module 245-*a* (or training data from which the thresholds can be identified) via the receiver module 305. Alternatively, the device 115-*b* may be pre-programmed with the thresholds, or the device 115-*b* may identify the thresholds from training data obtained via the skin conductance signal sensor 240-*a*.

The device 115-*b* may also receive web content, user input, or other data via the receiver module 305. The web content may be provided to the application module 325, which may determine whether and how a user of the device 115-*b* is aroused by the web content. In some cases, the web content may include advertisements that an advertiser desires to evaluate by means of user arousal assessment. The application module 325 may determine whether and how a user is aroused by causing the web content to be displayed to the user, and then acquiring or capturing a skin conductance response from the skin conductance processing module 245-*a*. A particular advertisement may be considered successful if it elicits a certain arousal level from an intended subject.

In other embodiments, the application module 325 can determine, for example, the user's arousal in response to photos captured or displayed by the device 115-*b*; to music, advertisements or other content played to the user; or to the user's interaction with a game played on the device 115-*b*.

By way of example, the transmitter module 315 may include one or more of a cellular transmitter or a WLAN transmitter. In some cases, the skin conductance signal or skin conductance response may be transmitted from the device, over a network, via the transmitter module 315.

Figure 4:
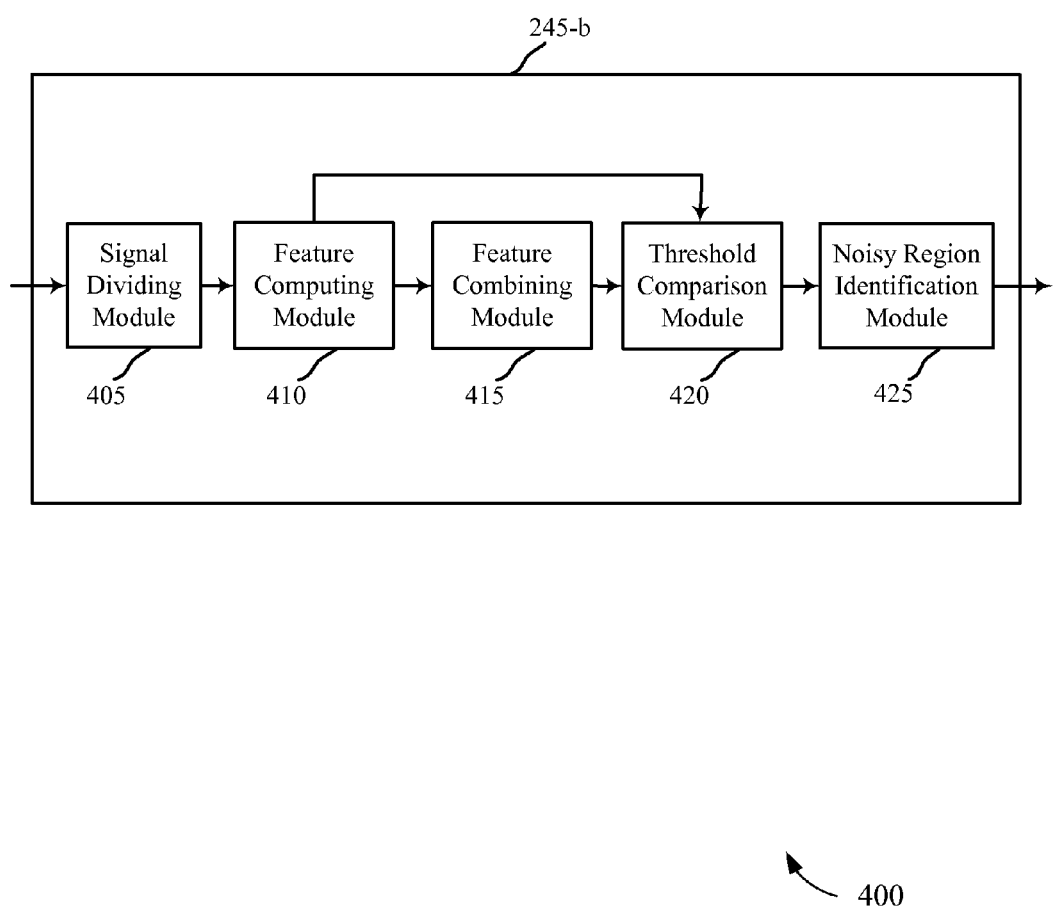
FIG. 4 is a block diagram of an example of a skin conductance signal processing module for identifying noisy regions in a skin conductance signal.

FIG. 4 is a block diagram 400 illustrating one embodiment of a skin conductance signal processing module 245-*b*. The module 245-*b* may be an example of the skin conductance signal processing module 245 shown in FIG. 2 and/or FIG. 3. The module 245-*b* may include a signal dividing module 405, a feature computing module 410, a feature combining module 415, a threshold comparison module 420, and a noisy region identification module 425. The module 245-*b* may be used to identify noisy regions in a skin conductance signal.

In one embodiment, the skin conductance signal processing module 245-*b* may acquire a skin conductance signal. The signal may be received by the receiver module 305 via one or more skin conductance sensors. The one or more sensors may be on-board a mobile device 115.

The signal dividing module 405 may divide the skin conductance signal into a plurality of windows. For example, the signal dividing module may receive the skin conductance signal as an ordered sequence of discrete samples, and may divide the signal into a plurality of windows such that each window includes one or more of the discrete samples (e.g., using a sliding window approach). In some embodiments, one or more samples of the skin conductance signal may be included in both a first window and a second window, such that the second window overlaps the first window. In some instances, all of the windows may overlap.

The feature computing module 410 may compute two or more features of the skin conductance signal within each window. At least one of the features may be in a frequency domain. One or more of the features may also be in a time domain. The computed features may include, for example, two or more of: a normalized range, a normalized maximum or minimum, a number of mean crossings, an amount of low frequency energy (e.g., the amount of energy below a signal mean), or an amount of high frequency energy (e.g., the amount of energy above the signal mean).

The feature combining module 415 may combine two or more of the features computed for a particular window to obtain at least a first metric for the window. For example, the amount of low frequency energy for a window may be combined with the amount of high frequency energy for the window to form a ratio of the amount of low frequency energy to the amount of high frequency energy (e.g., an LF/HF ratio).

The threshold comparison module 420 may compare each metric for a window to a corresponding threshold. For example, the module 420 may compare the LF/HF ratio for a window to an LF/HF ratio threshold. The threshold comparison module 420 may also compare the values of one or more features to corresponding thresholds. For example, the module 420 may compare the number of signal mean crossings to a corresponding mean crossing threshold.

The noisy region identification module 425 may identify a window as a noisy region of the skin conductance signal based on one or more of the comparisons. For example, in one embodiment, a window is identified as a noisy region when its LF/HF ratio exceeds a threshold indicating that its amount of high frequency energy is too great. In another example embodiment, a window is identified as a noisy region based on a combination of comparisons. For example, a window may be identified as a noisy region when both 1) its LF/HF ratio exceeds a threshold, and 2) its number of signal mean crossings exceeds a threshold. A combination of comparisons can mitigate the likelihood of a window being erroneously identified as a noisy region. Regions of the skin conductance signal that have been identified as noisy, may be ignored when determining the SCR.

Figure 5:
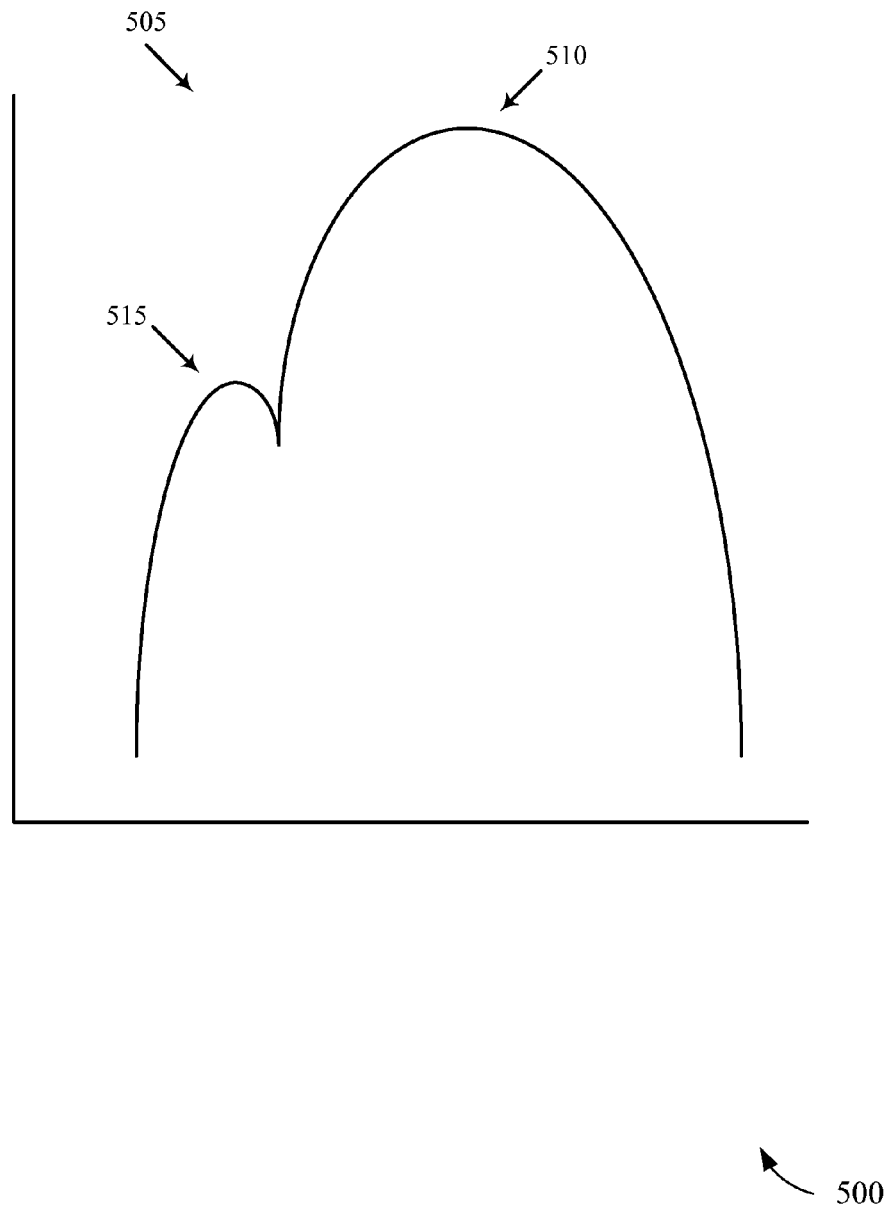
FIG. 5 provides a graph of an example of a complex peak pattern of a skin conductance signal.

FIG. 5 provides a graph 500 of a complex peak pattern. In some embodiments, the skin conductance signal processing module 245 described in FIGS. 2, 3, and/or 4 can be used to identify a complex peak pattern within a skin conductance signal. In the context of FIG. 5, current skin conductance response systems are configured to detect a primary peak 510 of a skin conductance signal 505, but fail to detect a secondary peak 515. However, the secondary peak 515 may indicate a change in a user's arousal, and may therefore provide useful information that prior systems, methods and apparatus for processing skin conductance signals are unable to detect. Details regarding the detection of primary and secondary peaks will be described below.

Figure 6:
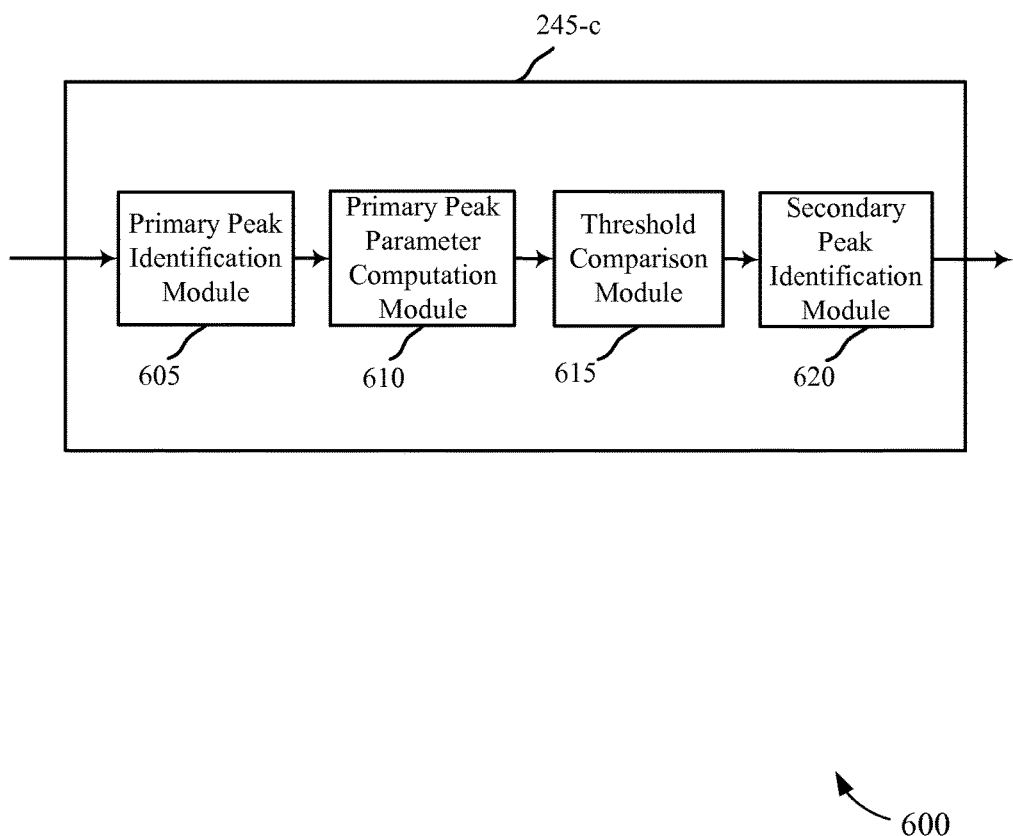
FIG. 6 is a block diagram of an example of a skin conductance signal processing module for detecting a skin conductance signal feature such as a complex peak pattern.

FIG. 6 is a block diagram 600 illustrating another embodiment of a skin conductance signal processing module 245-*c*. The module 245-*c* may be an example of the skin conductance signal processing module 245 shown in FIGS. 2, 3, and/or 4. The module 245-*c* may include a primary peak identification module 605, a primary peak parameter computation module 610, a threshold comparison module 615, and a secondary peak identification module 620. The module 245-*c* may be used to detect peaks of a skin conductance signal. The detected peaks can then be analyzed to determine a user's skin conductance response.

The primary peak identification module 605 may identify a first set of peaks of the skin conductance signal. The first set of peaks is identified by identifying a first set of one or more parameters of the skin conductance signal and comparing each parameter to a corresponding threshold in a first set of one or more thresholds. The parameters may include first derivatives of the discrete samples forming the skin conductance signal, as well as the rise times, amplitudes, and slopes of suspected peak edges. The identified first set of peaks includes one or more primary peaks of the skin conductance signal.

The primary peak parameter computation module 610 may compute a second set of one or more parameters for at least one primary peak in the identified first set of peaks. In some embodiments, the set of parameters may include a curvedness factor for each edge of each primary peak (e.g., a curvedness factor for each rising edge and each falling edge of each primary peak).

The threshold comparison module 615 may compare each parameter of the second set of parameters, including the curvedness factor, to a corresponding threshold in a second set of one or more thresholds.

The secondary peak identification module 620 may identify at least one secondary peak associated with the at least one primary peak based on the comparison of each parameter of the second set of one or more parameters to a corresponding threshold in a second set of one or more thresholds. In some embodiments, a secondary peak may be identified based solely on the curvedness of a primary peak's edges. In addition, the module 620 may identify a location of the secondary peak base on a change in sign in the second set of one or more parameters.

Figure 7:
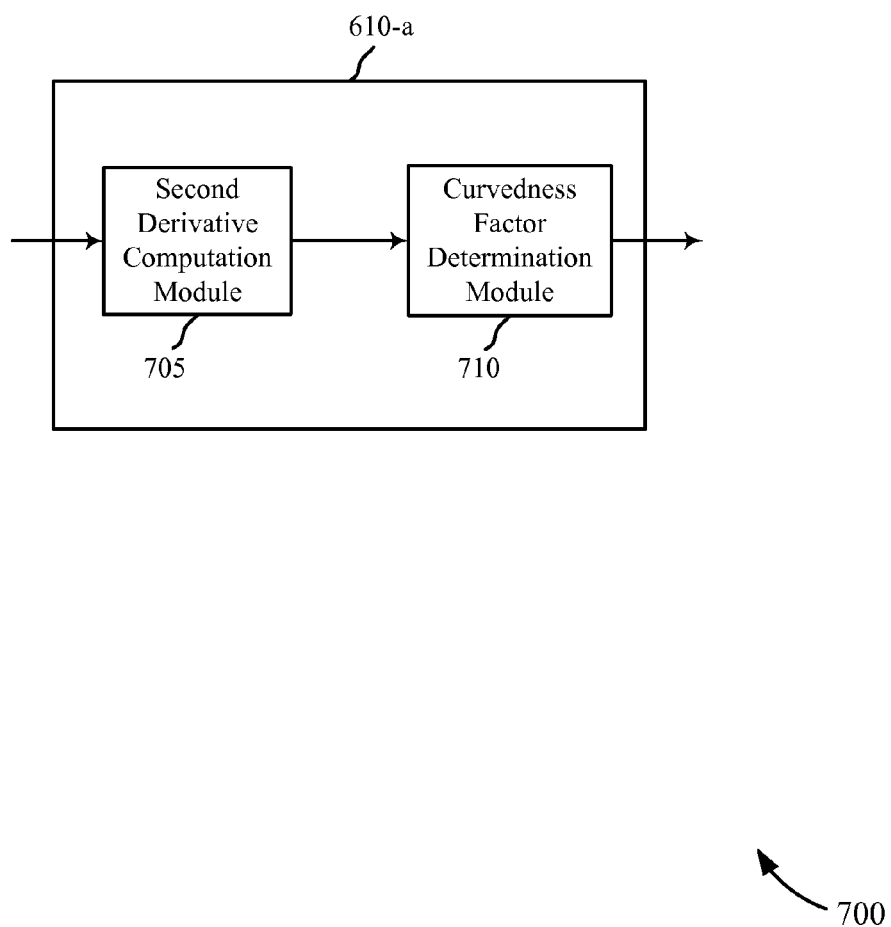
FIG. 7 is a block diagram of an example of a primary peak parameter computation module.

FIG. 7 is a block diagram 700 illustrating one embodiment of a primary peak parameter computation module 610-a. The module 610-a may be an example of the primary peak parameter computation module 610 described in FIG. 6. The module 610-a may include a second derivative computation module 705 and a curvedness factor determination module 710.

For each edge of each primary peak, the second derivative computation module 705 computes a set of second derivatives for the set of discrete samples located along the edge of the primary peak.

For each set of second derivatives, the curvedness factor determination module 710 determines a curvedness factor of the corresponding edge. This may be done by first determining a range of the set of second derivatives, and then identifying a magnitude of the range as the curvedness factor.

Figure 8:
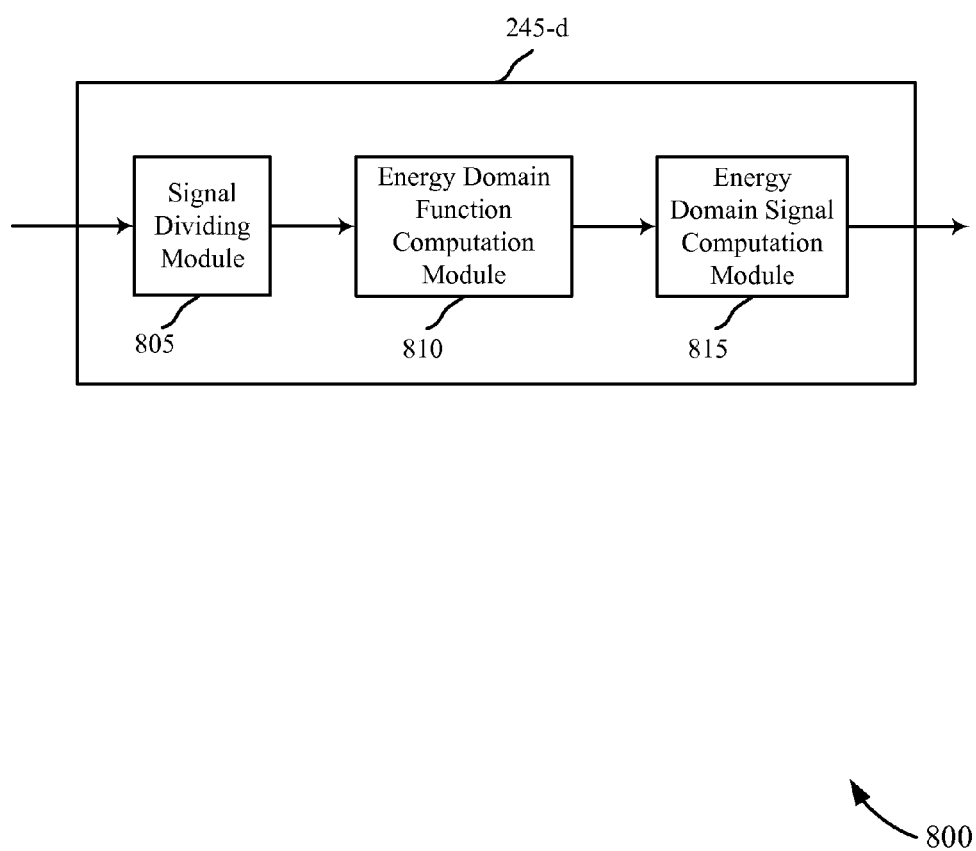
FIG. 8 is a block diagram of an example of a skin conductance signal processing module for converting a skin conductance signal from a time domain to an energy domain.

FIG. 8 is a block diagram 800 illustrating another embodiment of a skin conductance signal processing module 245-d. The module 245-d may be an example of the skin conductance signal processing module 245 described in FIGS. 2, 3, 4, and/or 6. The module 245-d may include a signal dividing module 805, an energy domain function computation module 810, and an energy domain signal computation module 815. The module 245-d may be used to convert a skin conductance signal from a time domain to an energy domain, thereby enabling the detection of signal features (e.g., peaks) that are not detectable in the time domain. The detected peaks can be analyzed to determine a user's skin conductance response.

Existing systems, methods and apparatus of processing skin conductance signals rely on the detection of temporal peaks in a skin conductance signal. This results in the rejection of portions or regions of the biophysical signal that may have small magnitudes in the time domain, even though in the energy domain, the peak may represent sufficient energy (e.g., sufficient instantaneous energy) to indicate arousal. Conversion of a skin conductance signal to an energy domain can therefore enable extraction of arousal information not discernible in the time domain.

The signal dividing module 805 may divide a skin conductance signal into a plurality of windows. For example, the signal dividing module may receive the skin conductance signal as an ordered sequence of discrete samples, and may divide the signal into a plurality of windows such that each window includes one or more of the discrete samples (e.g., using a sliding window approach). In some embodiments, one or more samples of the skin conductance signal may be included in both a first window and a second window, such that the second window overlaps the first window. In some instances, all of the windows may overlap.

The energy domain function computation module 810 may compute a function of the skin conductance signal for each window to obtain a corresponding metric of energy in the energy domain. For example, the module 810 may compute a first metric of energy for the skin conductance signal in a first window, a second metric of energy for the skin conductance signal in a second window, etc. In some embodiments, the function of the skin conductance signal may be computed as an area defined at least in part by a particular window and the skin conductance signal.

The energy domain signal computation module 815 computes a second signal in the energy domain. The second signal is a function of the metric of energy, and in some cases may be equal to the metric of energy. The second signal may be compared to a corresponding threshold to identify one or more peaks of the skin conductance signal in the energy domain.

Figure 9:
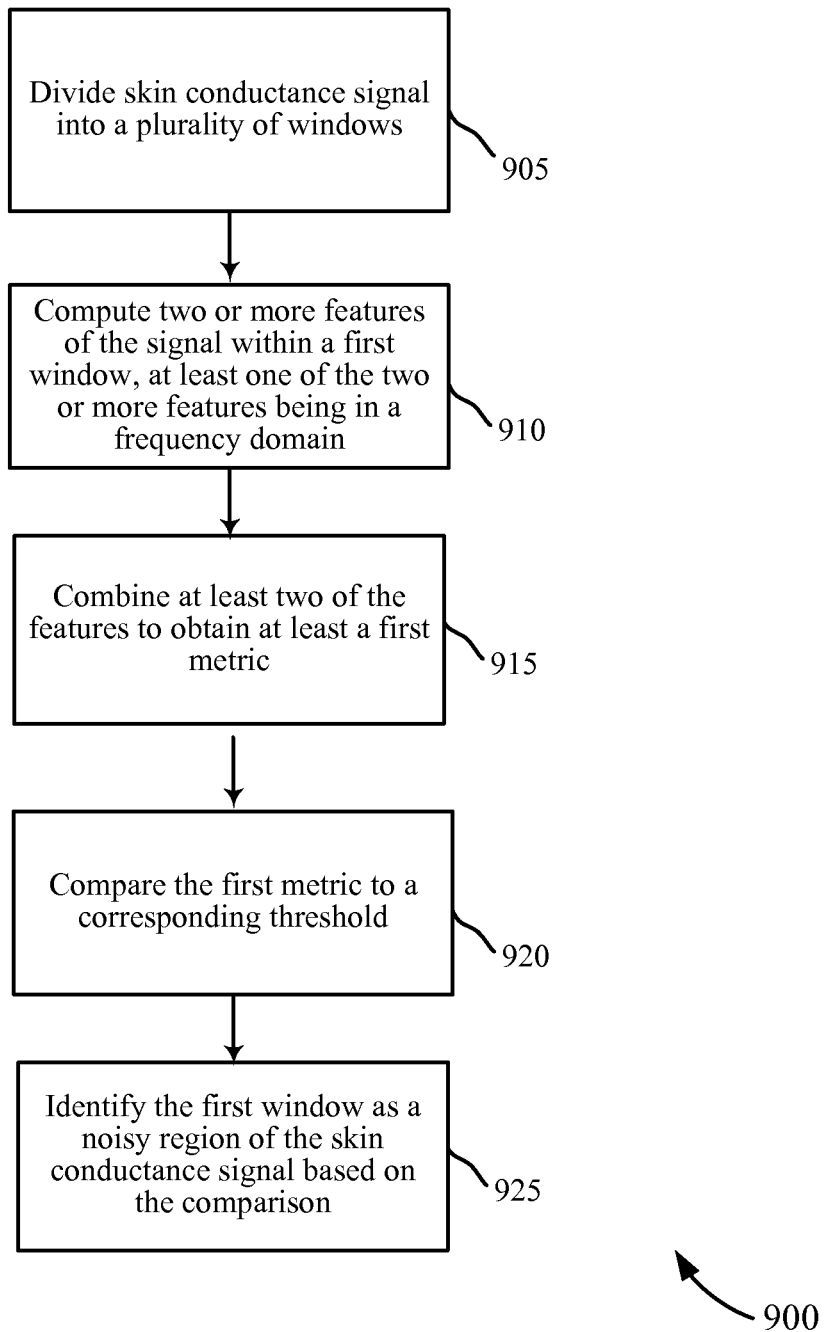
FIG. 9 is a flow chart of one example of a method for identifying noisy regions in a skin conductance signal.

FIG. 9 is a flow chart illustrating one example of a method 900 for identifying noisy regions in a skin conductance signal. For clarity, the method 900 is described below with reference to the mobile devices 115 shown in FIG. 1, 2 or 3. In one implementation, the skin conductance signal processing module 245 described in FIGS. 2, 3, 4, 6, and/or 8 may execute one or more sets of codes to control the functional elements of the mobile device 115 to perform the functions described below.

At block 905, the skin conductance signal is divided into a plurality of windows. For example, the signal may be an ordered sequence of discrete samples that are divided into a plurality of windows such that each window includes a plurality of the discrete samples. In some embodiments, one or more samples of the skin conductance signal may be included in both a first window and a second window, such that the second window overlaps the first window. In some instances, all of the windows may overlap.

At block 910, two or more features of the signal within a first window are computed. At least one of the two or more features is in a frequency domain. The computed features may include two or more of: a normalized range, a normalized maximum or minimum, a number of mean crossings, an amount of low frequency energy (e.g., the amount of energy below a signal mean), or an amount of high frequency energy (e.g., the amount of energy above the signal mean).

At block 915, at least two of the features are combined to obtain at least a first metric. For example, the amounts of low and high frequency energy may be combined to form an LF/HF ratio. At block 920, the first metric may be compared to a corresponding threshold. At block 925, the first window may be identified as a noisy region of the skin conductance signal based on the comparison.

Thus, the method 900 may provide an improved way for a mobile device 115 to identify noisy regions in a skin conductance signal. It should be noted that the method 900 is just one implementation and that the operations of the method 900 may be rearranged or otherwise modified such that other implementations are possible.

Figure 10:
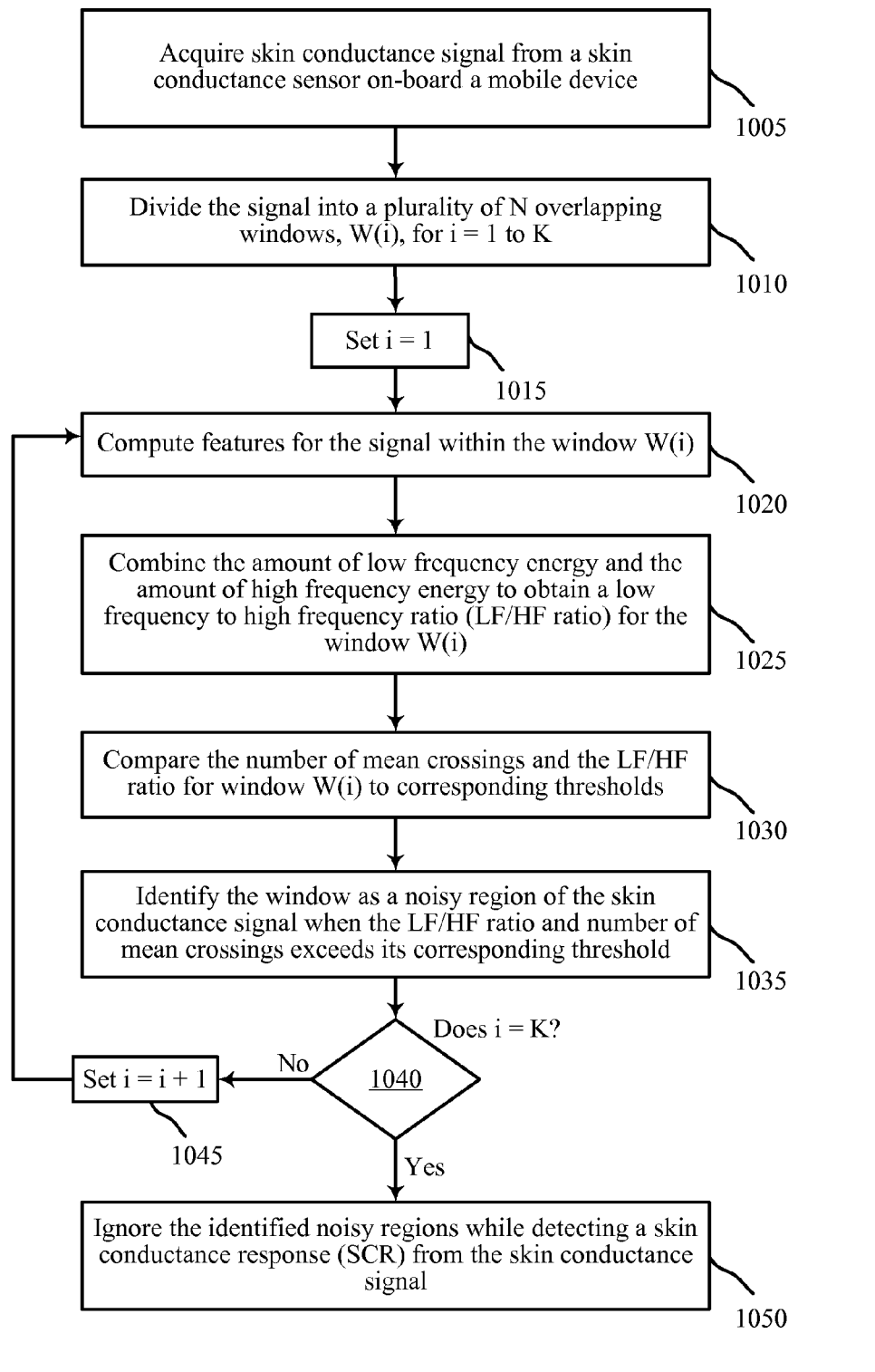
FIG. 10 is a flow chart of a second example of a method for identifying noisy regions in a skin conductance signal.

FIG. 10 is a flow chart illustrating another example of a method 1000 for identifying noisy regions in a skin conductance signal. For clarity, the method 1000 is described below with reference to one of the mobile devices 115 shown in FIGS. 1, 2 and/or 3. In one implementation, the skin conductance signal processing module 245 described in FIGS. 2, 3, 4, 6, and/or 8 may execute one or more sets of codes to control the functional elements of the mobile device 115 to perform the functions described below.

At block 1005, a skin conductance signal, x(n), is acquired from a skin conductance sensor on-board a mobile device. The signal may then be divided into a plurality of K overlapping windows, W(i), at block 1010. The windows may be generated using a sliding window approach. Each window may include N(i) samples of the signal x(n), and in some cases, N(i) may be equal to a constant N. In other cases, the windows W(i) may include different numbers of samples N(i).

Blocks 1020-1035 may be repeated for each window, W(i), for i=1 to K, as indicated by the variable setting and decision blocks 1015, 1040 and 1045. At block 1020, features of the skin conductance signal are computed. The computed features may comprise, for example, an amount of low frequency energy within the window W(i), an amount of high frequency energy within the window W(i), and a number of mean crossings within the window W(i). At block 1025, the amount of low frequency energy and the amount of high frequency energy are combined to obtain an LF/HF ratio for the window W(i). At block 1030, the number of mean crossings and the LF/HF ratio for the window W(i) are compared to corresponding thresholds. At block 1035, the window W(i) is identified as a noisy region of the skin conductance signal when the LF/HF ratio and number of mean crossings for the window both exceed corresponding thresholds.

At block 1050, the identified noisy region(s) are ignored while detecting a skin conductance response (SCR) from the skin conductance signal.

Thus, the method 1000 may provide an improved way for a mobile device 115 to identify noisy regions in a skin conductance signal. It should be noted that the method 1000 is just one implementation and that the operations of the method 1000 may be rearranged or otherwise modified such that other implementations are possible.

Figure 11:
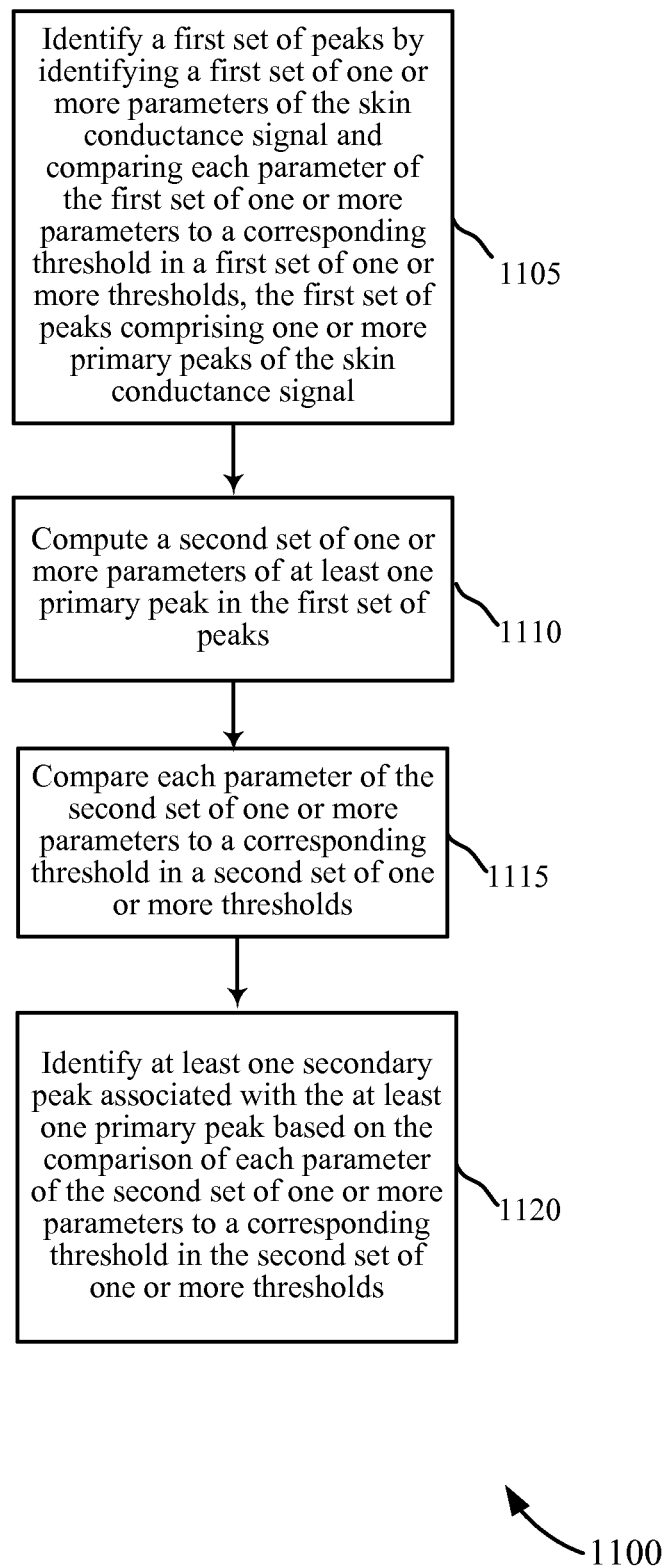
FIG. 11 is a flow chart of one example of a method for detecting a skin conductance signal feature such as a complex peak pattern.

FIG. 11 is a flow chart illustrating an example of a method 1100 for detecting peaks of a skin conductance signal. For clarity, the method 1100 is described below with reference to the mobile devices 115 shown in FIG. 1, 2 or 3. In one implementation, the skin conductance signal processing module 245 described in FIGS. 2, 3, 4, 6, and/or 8 may execute one or more sets of codes to control the functional elements of the mobile device 115 to perform the functions described below.

At block 1105, a first set of peaks is identified by identifying a first set of one or more parameters of the skin conductance signal and comparing each parameter of the first set of one or more parameters to a corresponding threshold in a first set of one or more thresholds. The first set of peaks includes one or more primary peaks of the skin conductance signal.

At block 1110, a second set of one or more parameters, of at least one primary peak in the first set of peaks, is computed. At block 1115, each parameter of the second set of one or more parameters is compared to a corresponding threshold in a second set of one or more thresholds. At block 1120, at least one secondary peak associated with the at least one primary peak is identified. The at least one secondary peak is identified based on the comparison of each parameter of the second set of one or more parameters to a corresponding threshold in the second set of one or more thresholds.

Thus, the method 1100 may provide an improved way for a mobile device 115 to identify peaks of a skin conductance signal. It should be noted that the method 1100 is just one implementation and that the operations of the method 1100 may be rearranged or otherwise modified such that other implementations are possible.

Figure 12:
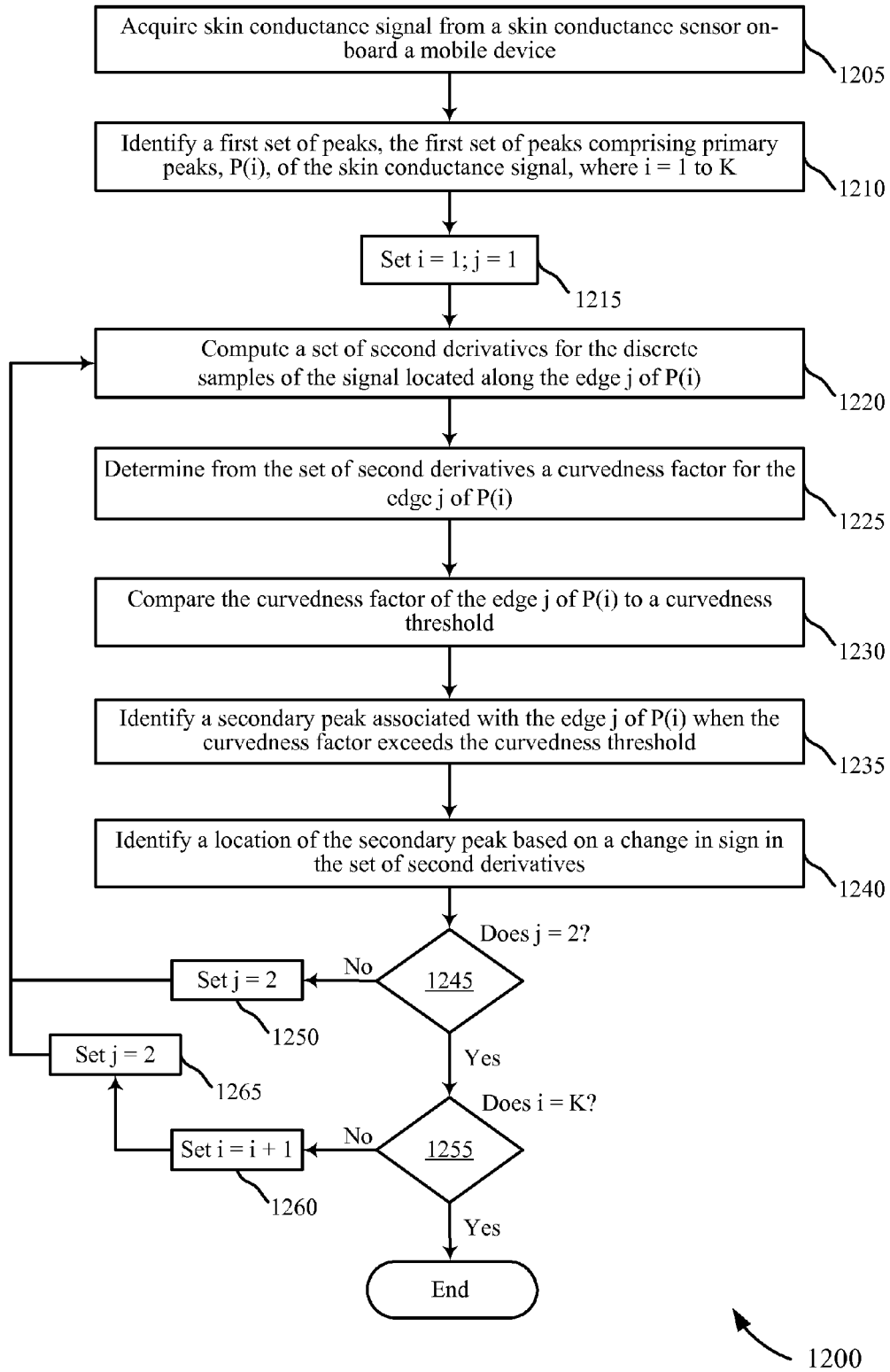
FIG. 12 is a flow chart of another example of a method for detecting a skin conductance signal feature such as a complex peak pattern.

FIG. 12 is a flow chart illustrating another example of a method 1200 for detecting peaks of a skin conductance signal. For clarity, the method 1200 is described below with reference to one of the mobile devices 115 shown in FIGS. 1, 2, and/or 3. In one implementation, the skin conductance signal processing module 245 shown in FIGS. 2, 3, 4, 6, and/or 8 may execute one or more sets of codes to control the functional elements of the mobile device 115 to perform the functions described below.

At block 1205, a skin conductance signal, x(n), is acquired from a skin conductance sensor on-board a mobile device 115. At block 1210, a first set of peaks is identified by identifying a first set of one or more parameters of the skin conductance signal and comparing each parameter of the first set of one or more parameters to a corresponding threshold in a first set of one or more thresholds. The first set of peaks includes one or more primary peaks, P(i), of the skin conductance signal.

Blocks 1220-1240 may be repeated for each primary peak, P(i), for i=1 to K, and for each edge j of each primary peak, as indicated by the variable setting and decision blocks 1215, 1245, 1250, 1255, 1260 and 1265. At block 1220, a set of second derivatives is computed for the discrete samples of the signal located along the edge j of peak P(i). At block 1225, a curvedness for the edge j of P(i) is determined from the set of second derivatives. The curvedness factor may be determined, in some cases, by first determining a range of the set of second derivatives, and then identifying a magnitude of the range as the curvedness factor. At block 1230, the curvedness factor of the edge j of P(i) is compared to a curvedness threshold, and at block 1235, a secondary peak associated with the edge j of P(i) is identified when the curvedness factor exceeds the curvedness threshold. At block 1240, a location of the secondary peak may be identified based on a change in sign in the set of second derivatives.

Thus, the method 1200 may provide an improved way for a mobile device 115 to identify peaks of a skin conductance signal. It should be noted that the method 1200 is just one implementation and that the operations of the method 1200 may be rearranged or otherwise modified such that other implementations are possible.

Figure 13:
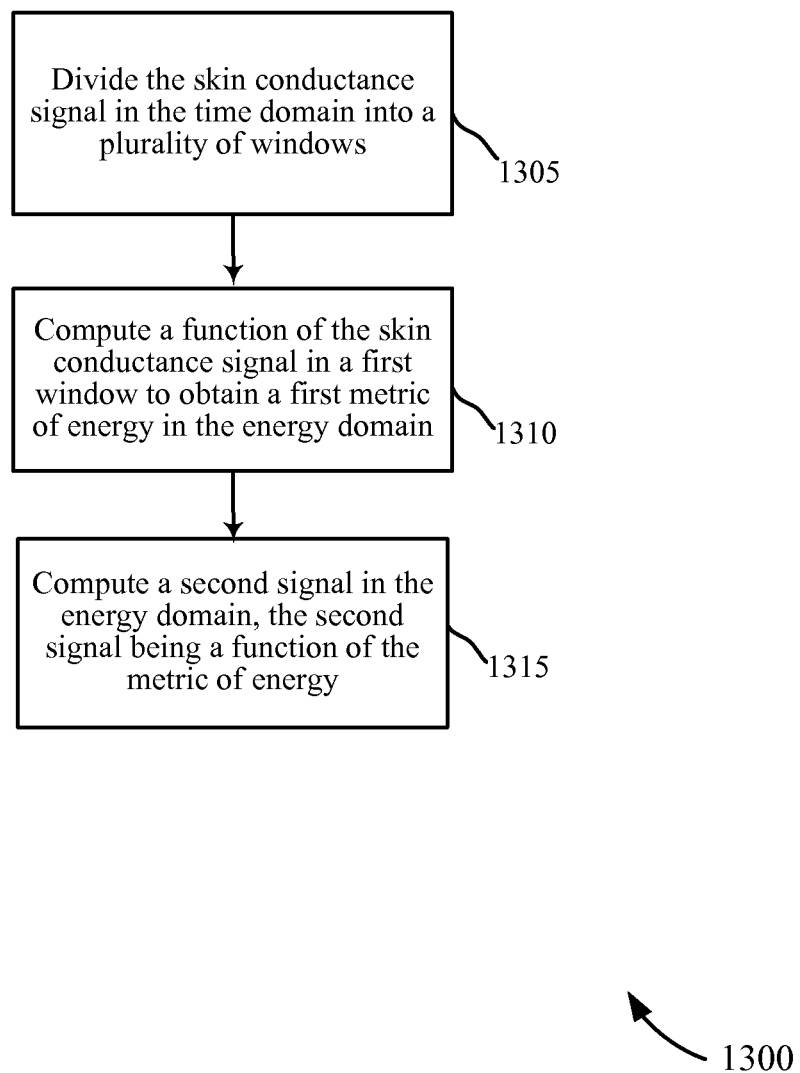
FIG. 13 is a flow chart of one example of a method for converting a skin conductance signal from a time domain to an energy domain.

FIG. 13 is a flow chart illustrating an example of a method 1300 for converting a skin conductance signal from a time domain to an energy domain. For clarity, the method 1300 is described below with reference to the mobile devices 115 shown in FIG. 1, 2 or 3. In one implementation, the skin conductance signal processing module 245 described in FIGS. 2, 3, 4, 6, and/or 8 may execute one or more sets of codes to control the functional elements of the mobile device 115 to perform the functions described below.

At block 1305, the skin conductance signal is divided into a plurality of windows. For example, the signal may be an ordered sequence of discrete samples that are divided into a plurality of windows such that each window includes a plurality of the discrete samples. In some embodiments, one or more samples of the skin conductance signal may be included in both a first window and a second window, such that the second window overlaps the first window. In some instances, all of the windows may overlap.

At block 1310, a function of the skin conductance signal may be computed in a first window to obtain a first metric of energy in the energy domain. In some embodiments, the function may be the area defined at least in part by the first window and the skin conductance signal. At block 1315, a second signal may be computed in the energy domain. The second signal is a function of the metric of energy.

Thus, the method 1300 may provide an improved way for a mobile device 115 to detect features of a skin conductance signal in an alternate domain, such as an energy domain. Such a method 1300 enables the identification of features that are non identifiable in the time domain. It should be noted that the method 1300 is just one implementation and that the operations of the method 1300 may be rearranged or otherwise modified such that other implementations are possible.

Figure 14:
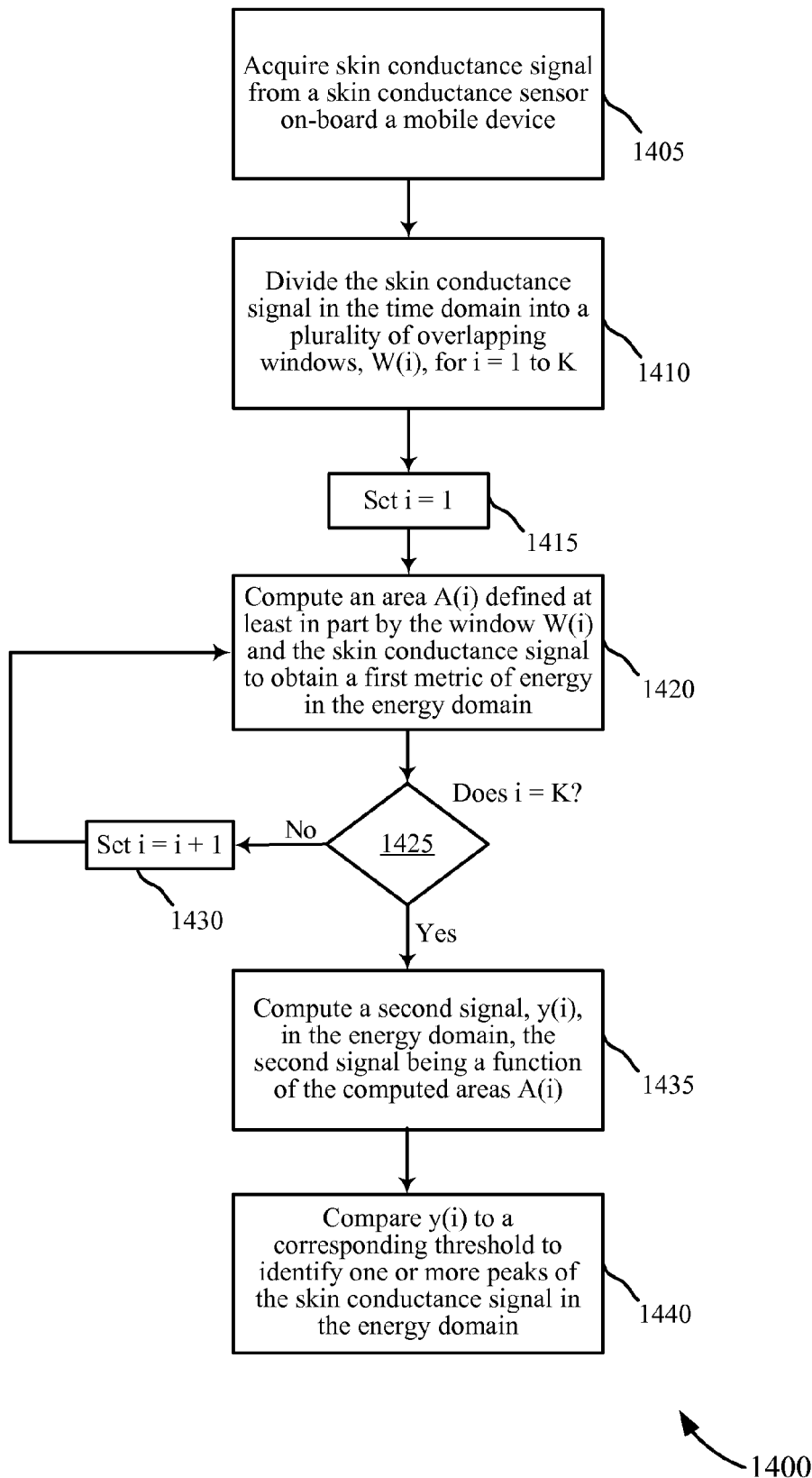
FIG. 14 is a flow chart of another example of a method for converting a skin conductance signal from a time domain to an energy domain.

FIG. 14 is a flow chart illustrating an example of a method 1400 for converting a skin conductance signal from a time domain to an energy domain. For clarity, the method 1400 is described below with reference to the mobile devices 115 shown in FIG. 1, 2 or 3. In one implementation, the skin conductance signal processing module 245 described in FIGS. 2, 3, 4, 6, and/or 8 may execute one or more sets of codes to control the functional elements of the mobile device 115 to perform the functions described below.

At block 1405, a skin conductance signal, x(n), may be acquired from a skin conductance sensor on-board a mobile device. The signal may then be divided into a plurality of K overlapping windows, W(i), at block 1410. The windows may be generated using a sliding window approach. Each window may include N(i) samples of the signal x(n), and in some cases, N(i) may be equal to a constant N. In other cases, the windows W(i) may include different numbers of samples N(i).

The operation at block 1420 is repeated for each window, W(i), for i=1 to K, as indicated by the variable setting and decision blocks 1415, 1425 and 1430. At block 1420, an area A(i) is computed for each window W(i). The area A(i) is defined at least in part by the window W(i) and the skin conductance signal. The area A(i) provides a metric of energy in the energy domain. In some cases, a low-pass filter may be applied to the signal x(n) for the purpose of adjusting the number of samples included in each window W(i) (e.g., the width of windows W(i)) and smoothing variations in the energy metric A(i). In this manner, the width of a second window may be adjusted to mitigate a variance between the metric A(i) for a first window and the metric A(i) for a second window.

At block 1435, a second signal, y(i), is computed in the energy domain. The second signal is a function of the computed areas A(i), and in some embodiments may be equal to A(i). At block 1440, the signal y(i) may be compared to a corresponding threshold, and a peak (or peaks) of the skin conductance signal in the energy domain may be identified based on the comparison. The identified peak(s) may provide information on user arousal.

Thus, the method 1400 may provide an improved way for a mobile device 115 to detect features of a skin conductance signal in an alternate domain, such as an energy domain. Such a method 1400 enables the identification of features that may be unidentifiable in the time domain. It should be noted that the method 1400 is just one implementation and that the operations of the method 1400 may be rearranged or otherwise modified such that other implementations are possible.

The detailed description set forth above in connection with the appended drawings describes exemplary embodiments and does not represent the only embodiments that may be implemented or that are within the scope of the claims. The term "exemplary" used throughout this description means "serving as an example, instance, or illustration," and not "preferred" or "advantageous over other embodiments." The detailed description includes specific details for the purpose of providing an understanding of the described techniques. These techniques, however, may be practiced without these specific details. In some instances, well-known structures and devices are shown in block diagram form in order to avoid obscuring the concepts of the described embodiments.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C).

Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

What is claimed is:

1. A method to identify noisy regions in a skin conductance signal, comprising:
    receiving, by a wireless device comprising a processor, the skin conductance signal based at least in part on a biofeedback device measurement associated with a subject;
    dividing, by the wireless device, the skin conductance signal into a plurality of windows;
    computing, by the wireless device, two or more features of the skin conductance signal within a first window, the two or more features including an amount of low frequency energy and an amount of high frequency energy within the first window, at least one of the two or more features being in a frequency domain;
    combining, by the wireless device, at least two of the two or more features of the skin conductance signal within the first window to obtain at least a first metric, the first metric being a ratio of the amount of low frequency energy to the amount of high frequency energy within the first window;
    comparing, by the wireless device, the first metric to a corresponding threshold;
    identifying, by the wireless device, the first window as a noisy region of the skin conductance signal based at least in part on the comparison; and
    transmitting, using a transceiver, a signal to a base station based at least in part on the identifying, wherein the signal indicates physiological data about the subject.

2. The method of claim 1, wherein the two or more features of the skin conductance signal comprise at least two of a normalized range, a normalized maximum or minimum, a number of mean crossings, an amount of low frequency energy, or an amount of high frequency energy.

3. The method of claim 1, further comprising:
    detecting a skin conductance response (SCR) from the skin conductance signal; and
    ignoring the identified noisy region of the skin conductance signal while detecting the SCR.

4. The method of claim 1, wherein each window comprises a plurality of discrete samples of the skin conductance signal.

5. The method of claim 4, wherein at least one of the plurality of discrete samples of the skin conductance signal is included in both the first window and a second window, such that the second window overlaps the first window.

6. The method of claim 1, wherein at least one of the two or more features is in a time domain.

7. The method of claim 1, wherein combining at least two of the two or more features to obtain at least the first metric comprises:
    combining a first feature in the frequency domain with a second feature in the frequency domain.

8. The method of claim 1, further comprising:
    presenting content; and
    evaluating the content based at least in part on the skin conductance signal.

9. The method of claim 1, further comprising:
    identifying the corresponding threshold for the first metric from training data.

10. The method of claim 9, wherein the training data is obtained from the skin conductance signal.

11. The method of claim 1, further comprising:
    comparing a value of at least one of the two or more features to a corresponding at least one additional threshold; and
    identifying the first window as a noisy region of the skin conductance signal based on a combination of the comparisons.

12. The method of claim 11, wherein comparing the value of at least one of the two or more features to the corresponding at least one additional threshold comprises:
    comparing a number of signal mean crossings to a corresponding mean crossing threshold; and
    identifying the first window as a noisy region of the skin conductance signal based on a combination of the comparisons.

13. The method of claim 1, further comprising:
    acquiring the skin conductance signal from a skin conductance sensor on-board a mobile device.

14. A mobile device for identifying noisy regions in a skin conductance signal, comprising:
    a processor;
    memory in electronic communication with the processor; and
    instructions stored in the memory, the instructions being executable by the processor to:
    receive the skin conductance signal based at least in part on a biofeedback device measurement associated with a subject;
    compute two or more features of the signal within a first window, the two or more features including an amount of low frequency energy and an amount of high frequency energy within the first window, at least one of the two or more features being in a frequency domain;
    combine at least two of the two or more features of the signal within the first window to obtain at least a first metric, the first metric being a ratio of the amount of low frequency energy to the amount of high frequency energy within the first window;
    compare the first metric to a corresponding threshold;
    identify the first window as a noisy region of the skin conductance signal based at least in part on the comparison; and
    transmitting, using a transceiver, a signal to a base station based at least in part on the identifying, wherein the signal indicates physiological data about the subject.

15. The mobile device of claim 14, wherein the two or more features of the skin conductance signal comprise at least two of a normalized range, a normalized maximum or minimum, a number of mean crossings, an amount of low frequency energy, or an amount of high frequency energy.

16. The mobile device of claim 14, wherein the instructions are further executable by the processor to:
present content; and
evaluate the content based at least in part on the skin conductance signal.

17. The mobile device of claim 14, wherein the instructions are further executable by the processor to:
acquire the skin conductance signal from one or more skin conductance sensors.

18. An apparatus comprising a processor for identifying noisy regions in a skin conductance signal, comprising:
means for receiving the skin conductance signal based at least in part on a biofeedback device measurement associated with a subject;
means for dividing the signal into a plurality of windows;
means for computing two or more features of the signal within a first window, at least one of the two or more features being in a frequency domain, the two or more features including an amount of low frequency energy and an amount of high frequency energy within the first window;
means for combining at least two of the two or more features of the signal within the first window to obtain at least a first metric, the first metric being a ratio of the amount of low frequency energy to the amount of high frequency energy within the first window;
means for comparing the first metric to a corresponding threshold;
means for identifying the first window as a noisy region of the skin conductance signal based at least in part on the comparison; and
means for transmitting, using a transceiver, a signal to a base station based at least in part on the identifying, wherein the signal indicates physiological data about the subject.

19. The apparatus of claim 18, wherein the two or more features of the skin conductance signal comprise at least two of a normalized range, a normalized maximum or minimum, a number of mean crossings, an amount of low frequency energy, or an amount of high frequency energy.

20. The apparatus of claim 18, further comprising:
means for presenting content; and
means for evaluating the content based at least in part on the skin conductance signal.

21. The apparatus of claim 18, further comprising:
means for acquiring the skin conductance signal from a skin conductance sensor on-board the mobile device.

22. A non-transitory computer-readable medium storing instructions executable by a processor to:
receive a skin conductance signal based at least in part on a biofeedback device measurement associated with a subject;
divide the skin conductance signal into a plurality of windows;
compute two or more features of the skin conductance signal within a first window, the two or more features including an amount of low frequency energy and an amount of high frequency energy within the first window, at least one of the two or more features being in a frequency domain;
combine at least two of the two or more features of the skin conductance signal within the first window to obtain at least a first metric, the first metric being a ratio of the amount of low frequency energy to the amount of high frequency energy within the first window;
compare the first metric to a corresponding threshold;
identify the first window as a noisy region of the skin conductance signal based at least in part on the comparison; and
transmit, using a transceiver, a signal to a base station based at least in part on the identifying, wherein the signal indicates physiological data about the subject.

23. The computer program product of claim 22, wherein the two or more features of the skin conductance signal comprise at least two of a normalized range, a normalized maximum or minimum, a number of mean crossings, an amount of low frequency energy, or an amount of high frequency energy.

24. The computer program product of claim 22, wherein the instructions are further executable by the processor to:
present content; and
evaluate the content based at least in part on the skin conductance signal.

25. A method to convert a skin conductance signal from a time domain to an energy domain, comprising:
receive, by a wireless device comprising a processor, the skin conductance signal based at least in part on a biofeedback device measurement associated with a subject;
computing, by the wireless device, a function of the skin conductance signal in a first window to obtain a first metric of energy in the energy domain;
computing, by the wireless device, the function of the skin conductance signal in a second window to obtain a second metric of energy in the energy domain;
adjusting, by the wireless device, a width of the second window to mitigate a variance between the first metric of energy and the second metric of energy;
computing, by the wireless device, a signal in the energy domain, the signal being a function of the first metric of energy, the second metric of energy, or a combination thereof; and
transmitting to a base station, using a transceiver, an indication of physiological data of the subject, wherein the indication is based at least in part on the computed signal.

26. The method of claim 25, wherein each window comprises a plurality of discrete samples of the skin conductance signal.

27. The method of claim 26, wherein at least one of the plurality of discrete samples of the skin conductance signal is included in overlapping windows of the plurality of windows.

28. The method of claim 25, wherein computing the function of the skin conductance signal in the first window to obtain the first metric of energy in the energy domain comprises:
computing an area defined at least in part by the first window and the skin conductance signal.

29. The method of claim 28, further comprising:
comparing the signal to a corresponding threshold; and
identifying a peak of the skin conductance signal in the energy domain based on the comparison.

30. The method of claim 25, further comprising:
acquiring the skin conductance signal from a skin conductance sensor on-board a mobile device.

31. A mobile device for converting a skin conductance signal from a time domain to an energy domain, comprising:
a processor;
memory in electronic communication with the processor; and
instructions stored in the memory, the instructions being executable by the processor to:

receive the skin conductance signal based at least in part on a biofeedback device measurement associated with a subject;

compute a function of the skin conductance signal in a first window to obtain a first metric of energy in the energy domain;

compute the function of the skin conductance signal in a second window to obtain a second metric of energy in the energy domain;

adjust a width of the second window to mitigate a variance between the first metric of energy and the second metric of energy;

compute a signal in the energy domain, the signal being a function of the first metric of energy, the second metric of energy, or a combination thereof; and transmit to a base station, using a transceiver, an indication of physiological data of the subject, wherein the indication is based at least in part on the computed signal.

32. An apparatus comprising a processor for converting a skin conductance signal from a time domain to an energy domain, comprising:

means for receiving the skin conductance signal based at least in part on a biofeedback device measurement associated with a subject;

means for dividing the skin conductance signal in the time domain into a plurality of windows;

means for computing a function of the skin conductance signal in a first window to obtain a first metric of energy in the energy domain;

means for computing the function of the skin conductance signal in a second window to obtain a second metric of energy in the energy domain;

means for adjusting a width of the second window to mitigate a variance between the first metric of energy and the second metric of energy;

means for computing a signal in the energy domain, the signal being a function of the first metric of energy, the second metric of energy, or a combination thereof; and means for transmitting to a base station, using a transceiver, an indication of physiological data of the subject, wherein the indication is based at least in part on the computed signal.

33. A non-transitory computer-readable medium storing instructions executable by a processor to:

divide a skin conductance signal in the time domain into a plurality of windows;

compute a function of the skin conductance signal in a first window to obtain a first metric of energy in the energy domain;

compute the function of the skin conductance signal in a second window to obtain a second metric of energy in the energy domain;

adjust a width of the second window to mitigate a variance between the first metric of energy and the second metric of energy; and compute a signal in the energy domain, the signal being a function of the first metric of energy, the second metric of energy, or a combination thereof; and transmit to a base station, using a transceiver, an indication of physiological data of the subject, wherein the indication is based at least in part on the computed signal.

* * * * *